United States Patent [19]

Sims

[11] Patent Number: 5,104,214
[45] Date of Patent: Apr. 14, 1992

[54] TRIAL FRAMES, ADJUSTABLE SPECTACLES AND ASSOCIATED LENS SYSTEMS

[76] Inventor: Clinton N. Sims, 3432 W. Riverside Dr., Ft. Myers, Fla. 33901

[21] Appl. No.: 427,724

[22] Filed: Oct. 27, 1989

Related U.S. Application Data

[63] Continuation-in-part of Ser. No. 310,334, Feb. 13, 1989, Pat. No. 4,943,162, which is a continuation-in-part of Ser. No. 116,322, Nov. 2, 1987, Pat. No. 4,840,479, which is a continuation-in-part of Ser. No. 23,980, Mar. 16, 1987, Pat. No. 4,820,040, which is a continuation of Ser. No. 670,398, Nov. 9, 1984.

[51] Int. Cl.⁵ ............................................. A61B 3/02
[52] U.S. Cl. ..................................... 351/235; 351/229
[58] Field of Search ............... 351/229, 231, 233, 234, 351/235, 246, 227, 228; 350/433, 434, 247

[56] References Cited

U.S. PATENT DOCUMENTS

| | | |
|---|---|---|
| 1,222,017 | 4/1917 | Moseley . |
| 1,266,224 | 5/1918 | Day . |
| 1,337,265 | 4/1920 | Poser . |
| 1,457,494 | 6/1923 | Bugbee ............................ 351/229 |
| 1,550,582 | 8/1925 | Sheard ............................ 351/229 |
| 1,594,196 | 7/1926 | Herold et al. . |
| 1,611,167 | 12/1926 | DeZeng . |
| 1,794,571 | 3/1931 | Wrighton et al. . |
| 2,147,448 | 2/1939 | Lee . |
| 2,256,491 | 9/1941 | Peck et al. . |
| 2,333,738 | 11/1943 | Peck et al. . |
| 3,822,932 | 7/1974 | Humphrey . |

OTHER PUBLICATIONS

Page 438 in Volume 5 of "System of Ophthalmology", entitled, *Ophthalmic Optics and Refraction*, by Duek--Elder and Agrams (1970).

*Primary Examiner*—Rodney B. Bovernick
*Attorney, Agent, or Firm*—Kilpatrick & Cody

[57] ABSTRACT

Trial frames including two independently rotatable cells alignable with each eye are disclosed. Each set of cells is designed to house a pair of either cylinder, polarized, prism, crossed cylinder or sphero-cylinder lenses as appropriate for correcting optical errors such as astigmatism, macular defects, or diplopia. Because the lenses associated with the cells are designed to rotate independently, no synchorinized gear mechanism is required. Moreover, because axes throughout the entire visual field may be generated using independent rotation of two lenses, the batteries of trial lenses used in connection with conventional trial frames need not be used. Adjustable spectacles and an alternative lens system also are disclosed. The adjustable spectacles are particularly useful for persons whose refractive error is changing relatively rapidly over a short period of time (such as persons recovering from cataract surgery) and who therefore cannot practically use conventional glasses or contact lenses. The lens systems may easily be adapted for use in the oculars of microscopes, telescopes, cameras, binoculars, kaleidoscopes, slit lamps, and other similar devices.

14 Claims, 2 Drawing Sheets

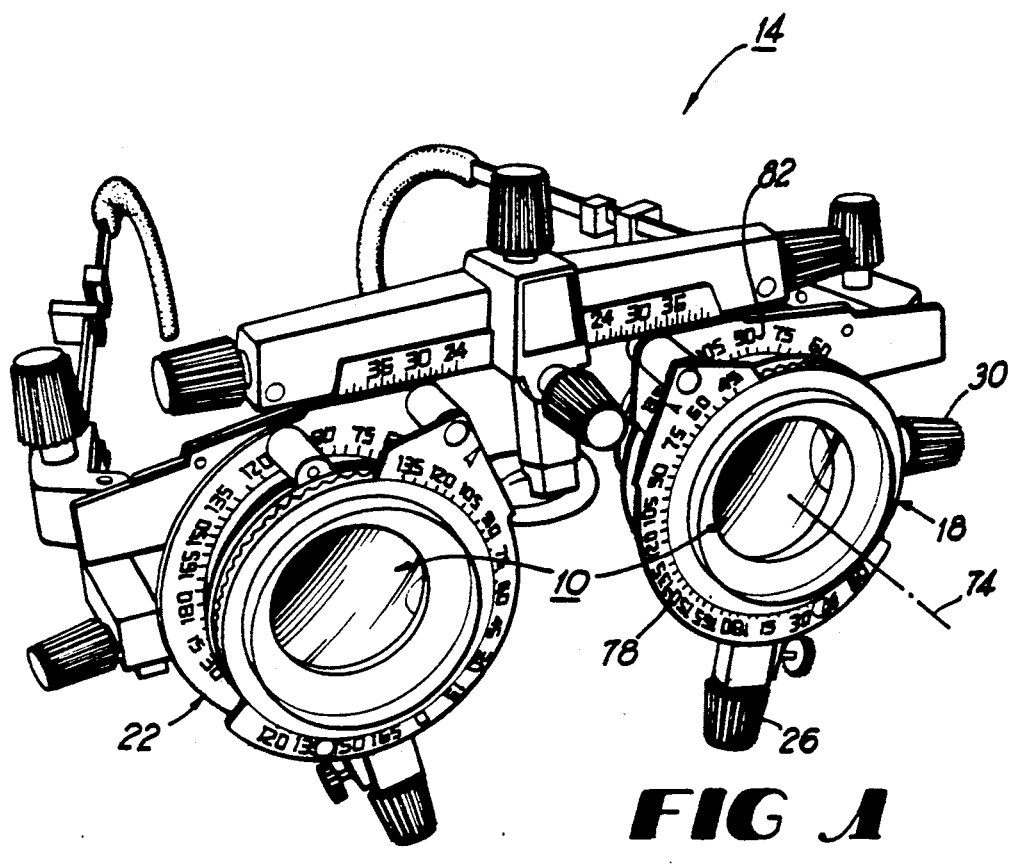

TRIAL FRAMES, ADJUSTABLE SPECTACLES AND ASSOCIATED LENS SYSTEMS

CROSS-REFERENCE TO RELATED APPLICATION

This application is a continuation-in-part of application Ser. No. 07/310,334, filed Feb. 13, 1989, entitled "Astigmatic Self-Refractor and Method of Use," now U.S. Pat. No. 4,943,162 which application is a continuation-in-part of application Ser. No. 07/116,322 (now U.S. Pat. No. 4,840,479), filed Nov. 2, 1987, entitled "Crossed Cylinder Lenses Refractor with Three-lens Variable Crossed Cylinder Assembly and Method of Use," which application is a continuation-in-part of application Ser. No. 07/023,980 (now U.S. Pat. No. 4,820,040), filed Mar. 16, 1987, entitled "Crossed Cylinder Lenses Refractor and Method of Use," which application is a continuation of application Ser. No. 06/670,398, filed Nov. 9, 1984, now abandoned of which applications are incorporated herein in their entireties by this reference.

FIELD OF THE INVENTION

This invention relates to subjective devices and associated lens systems for measuring or correcting optical errors in the eyes of humans.

BACKGROUND OF THE INVENTION

A variety of lens systems have been designed to produce variable crossed cylinder powers for measuring or correcting astigmatic errors through the use of refractors. One such lens structure, the Snellen-Stokes system, uses two counter-rotating cylinder lenses of equal power and opposite sign to produce variable crossed cylinder powers. A second system, disclosed by Humphrey in U.S. Pat. No. 3,822,932, utilizes two pairs of Snellen-Stokes lenses, with the combined lens axis of one pair offset 45° from the combined lens axis of the other pair. The pairs are alternatively counter-rotated to produce a desired combined cylinder power at a desired angle. Finally, a novel system described in my patent application Ser. No. 07/310,334 teaches use of four rotatable cylinder lenses of equal power and sign and a stationary lens of double the power and opposite sign of each of the cylinder lenses, to produce variable crossed-cylinder powers at various angles.

Diplopic errors typically are measured using two pairs of Risley prisms, with one pair aligned with each eye. Each Risley prism pair consists of two equal power prism lenses and is counter-rotated until fusion is obtained. The amount of rotation for one of the pairs of Risley prisms is related to the amount of base up/down defect present in the patient's eyes, while the rotation of the other pair corresponds to the base in/out defect present.

Each of the systems described above produces various optical powers through counter-rotation of pairs of lenses. Achieving counter-rotation, typically desired at equal rates in opposite directions, requires some type of timing mechanism such as a synchronized gear set. Consequently, no existing system is capable of generating crossed-cylinders throughout the 180° field without using synchronized rotation of two or more lenses. Moreover, no existing variable prism system can be used to correct diplopia without resort to counter-rotation of multiple pairs of prism lenses.

Conventional trial frames, used to measure and correct a variety of refractive errors, similarly lack means for rotating two cylinder lenses independently. U.S. Pat. No. 1,337,265, for example, discloses trial frames having a pair of lens carriers alignable with a patient's eyes. Each lens carrier includes three open pockets in which up to one sphere, cylinder and prism lens from a battery of lenses may be placed. In accordance with conventional refracting techniques, however, only the pocket containing the single cylinder lens may be rotated. Although such trial frames do not compel synchronized rotation of two or more lenses, they require use of batteries of lenses and are incapable of generating variable crossed-cylinder powers throughout the 0°180° visual field.

U.S. Pat. Nos. 2,256,491 and 2,333,738 disclose alternative trial frames designs. Again, however, these trial frames include only a single rotation mechanism for each lens carrier, precluding independent rotation of more than one cylinder lens associated with each eye.

SUMMARY OF THE INVENTION

The trial frames of the present invention include two independently rotatable cells alignable with each eye. Each cell is designed to house either a cylinder, polarized, prism, crossed cylinder or sphero-cylinder lens depending on the results sought to be achieved. Using two independently rotatable cylinder lenses in the two cells, for example, allows generation of varying crossed-cylinder powers throughout the entire visual field for measuring or correcting astigmatism. Polarized lenses may be used with the trial frames to detect macular defects, while a single pair of prism lenses may be used to detect and neutralize diplopia. The present trial frames also may be adapted for use as temporary spectacles by persons having refractive errors which change over a relatively short period of time, such as those recovering from cataract surgery. The patient need merely adjust the two cylinder, crossed cylinder, or sphero-cylinder lenses associated with each eye as needed until his or her vision stabilizes and more permanent spectacles or contact lenses can be prescribed. If desired, the trial frames may include accessory clips for positioning additional lenses of any type in the patient's line-of-sight.

The present trial frames offer at least two distinct advantages over existing frames. First, they allow patients to determine the appropriate astigmatic refractive or other optical correction for each eye merely by independently and alternatively rotating each of a pair of lenses. This process, akin to tuning a radio receiver, provides a reliable method for subjectively ascertaining the correction necessary without resort to batteries of trial lenses. Successful neutralization of refractive error by alternative independent rotation of lenses is a surprising result, as the rotation changes both the resulting power and axis, contrary to the result achieved through counter-rotation of lenses. Second, because the lens system used in conjunction with the novel trial frames differs from those requiring counter-rotation of various lenses, no synchronized gear system is needed for the present invention. The absence of synchronized gearing decreases the manufacturing cost, complexity, and weight of the present invention.

Also disclosed as part of the present invention is a three-lens system adaptable for use with modified trial frames or in the oculars of microscopes, telescopes, cameras, binoculars, kaleidoscopes, slit lamps, and other similar devices which require humans to view an image through an aperture positioned near one or both eyes. Alternatively, the lens system may be used in refractors similar to those discussed in my pending patent application Ser. No. 07/310,334 or in connection with a stand-alone instrument. The system includes two independently rotatable cylinder lenses and a sphero-cylinder lens which may be rotated ±90°. In some cases, however, as with oculars already having an adjustable sphere lens, the sphero-cylinder lens may be omitted. In such situations the invention would include merely two independently rotatable cylinder lenses of equal power but opposite sign or of the same power and sign.

It is therefore an object of the present invention to provide trial frames utilizing pairs of independently rotatable lenses associated with one or both eyes for correcting a variety of optical errors.

It is an additional object of the present invention to provide lens systems capable of generating crossed-cylinder and other powers at angles throughout the visual field without requiring counter-rotation of pairs of lenses.

It is another object of the present invention to provide a mechanism for detecting and neutralizing diplopic errors using a single pair of independently rotating lenses.

It is an additional object of the present invention to provide temporary spectacles for persons whose refractive error is changing relatively rapidly over a short period of time.

It is yet another object of the present invention to provide lens systems easily adaptable for use in the oculars of devices which present an image difficult to view while wearing conventional spectacles.

Other objects, features, and advantages of the present invention will become apparent with reference to the remainder of the written portion and the drawings of this application.

BRIEF DESCRIPTION OF THE DRAWINGS

FIG. 1 is a perspective view of the trial frames of the present invention.

FIG. 2 is a front elevational view of the trial frames of FIG. 1 with the right eye frame partially broken away.

DETAILED DESCRIPTION OF THE DRAWINGS

Figure 3:
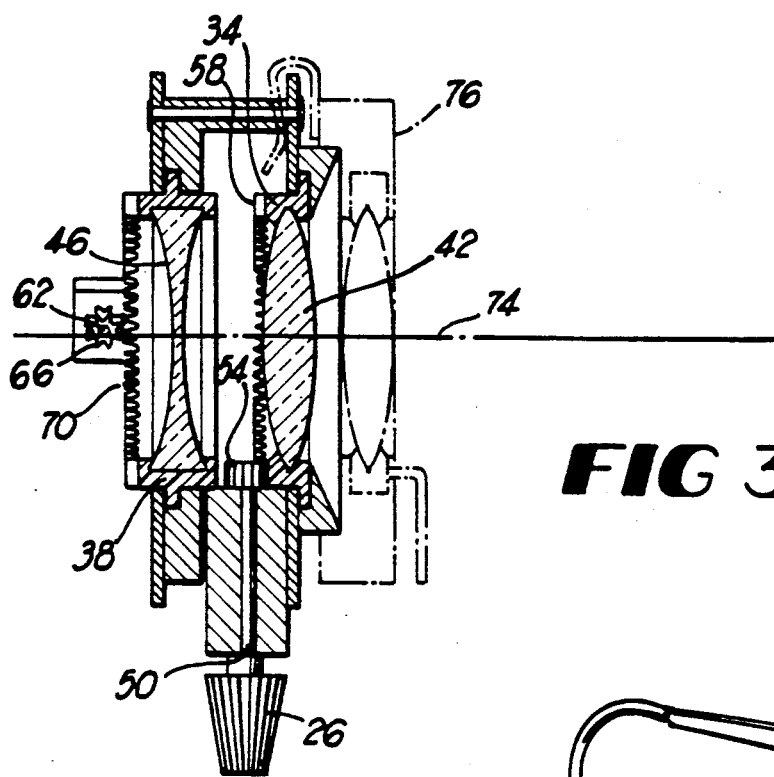
FIG. 3 is a cross-sectional view taken along lines 3—3 in FIG. 2.

FIGS. 1-3 illustrate a lens system 10 incorporated into the trial frames 14 of the present invention. Trial frames 14 may be worn by a patient having refractive error in one or both eyes and includes a right eye frame 18 and a left eye frame 22 (with "right" and "left" determined from the refractionist's point of view). These eye frames 18 and 22 may be essentially mirror images. If the two-frame trial frames 14 of FIGS. 1-3 are used, lens system 10 may be incorporated into both the right eye frame 18 and the left eye frame 22. Trial frames 14 need only include one eye frame, however, as only one eye need be refracted at a time. Because the right and left eyes may be refracted separately and the internal structure of right and left eye frames 18 and 22 are essentially identical, only the structure of right eye frame 18 will be described.

In accordance with the present invention trial frames 14 also include knobs 26 and 30 and rotary cells 34 and 38 associated with right eye frame 18 (and equivalent knobs and rotary cells associated with left eye frame 22). Rotary cells 34 and 38 contain lenses 42 and 46, respectively, which typically may be a pair of cylinder, polarized, prism, crossed cylinder, or sphero-cylinder lenses. Knob 26 forms one end of rod 50; the other end carries end gear 54 which meshes with a circular rack 58 encircling rotary cell 34 and controls the rotation of lens 42. Similarly, rod 62 contains knob 30 at one end and carries end gear 66 at the other, which gear 66 meshes with a circular rack 70 of rotary cell 38 and controls the rotation of lens 46. As those skilled in the art will recognize, however, any suitable devices for rotating lenses 42 and 46 may be used in place of the knobs and gears illustrated. In particular, rotational control of the lenses may be combined with existing controls if lenses 42 and 46 are incorporated into the oculars of microscopes, telescopes, cameras, binoculars, kaleidoscopes, slit lamps, and other similar devices rather than in trial frames 14.

Trial frames 14 also may include means for allowing adjustment to accommodate, for example, the differing facial and interpupilar requirements of individuals so that lenses 42 and 46 may be positioned along line-of-sight 74 of the patient's right eye. Various mechanisms for adjusting trial frames in these manners are illustrated in U.S. Pat. Nos. 1,794,571; 2,147,448; 2,256,491; and 2,333,738, all of which patents are incorporated herein in their entireties by this reference. Auxiliary lens holders such as those described in U.S. Pat. Nos. 2,256,491 and 2,333,738 or conventional accessory clips 76 (shown in phantom lines connected only to right eye frame 18 in FIG. 3, but connectable to left eye frame 22 as well), may be used to position additional lenses along line-of-sight 74. If trial frames 14 are to be used for multiple applications, rotary cells 34 and 38 may be designed to allow differing lens types to be substituted quickly and easily. Such substitution could be accomplished, for example, by crafting rotary cells 34 and 38 to include a spring mechanism for snapping lenses 42 and 46 in and out of place.

Operation of trial frames 14, again described with reference to right eye frame 18, is straightforward. If trial frames 14 are to be used for measuring or correcting astigmatism, cylinder or crossed cylinder lenses of equal power and opposite sign typically are chosen for lenses 42 and 46. With the lenses 42 and 46 in their unrotated positions (so that the sum of their powers is 0.00 D), the sphere lens providing the clearest vision for the patient is determined using any appropriate technique, including, for example, conventional methods involving a refractor or variable telescopic lens device having a sphere lens assembly. The appropriate sphere lens then may be placed in an accessory clip 76 associated with trial frames 14, if one is present, or the patient may be instructed to continue looking through the refractor. Once the most satisfactory sphere power is determined and positioned in line-of-sight 74, the patient may merely rotate knobs 26 and 30 independently and alternatively until the best visual acuity is obtained. A lensometer or degree scales 78 and 82 (FIGS. 1-2) associated with lenses 42 and 46 may be used in conjunction with a suitable chart or digital computer to measure the power and axis of the resulting crossed cylinder. Operation of the same lens system 10 including cylinder or crossed cylinder lenses positioned in the oculars of various devices is equally straightforward, with the viewer similarly merely rotating the lenses until the clearest vision is obtained.

Choosing polarized lenses for lenses 42 and 46 permits trial frames 14 to be used for detecting macular defects by performing reproducible Amsler grid tests. The patient's refractive error may be determined as described above, and the equivalent lenses placed in accessory clip 76. Polarization of lenses 42 and 46 may be controlled in such cases by referring to the degree scale 78 or 82 associated with either of lenses 42 or 46 while the axis of the other of lenses 42 or 46 remains fixed.

Diplopia may be detected and neutralized using trial frames 24 having prism lenses serving as lenses 42 and 46. Unlike the preceding techniques, however, which may be performed either on one eye at a time or on both eyes concurrently, detection of diplopia using standard exams such as the red lens or Maddox rod tests must be performed with the prism lenses in the line-of-sight of only one eye. With lenses correcting the refractive error placed in accessory clip 76 and the prisms placed in their unrotated positions (with the resulting power equal to 0.00 D), the patient merely rotates the two prism lenses independently and alternatively until fusion is obtained.

Typical values for lenses 42 and 46 include $-3.00 \times 180°$ D and $+3.00 \times 180°$ D when trial frames 14 are used for measuring astigmatism. Plano-polarized lenses may be used for detecting macular defects, and 3.00 D prism lenses may be utilized when a patient is tested for diplopia. Those skilled in the art will recognize, however, that the values may be modified depending on the needs of each patient without degrading the performance of the present invention.

Figure 4:
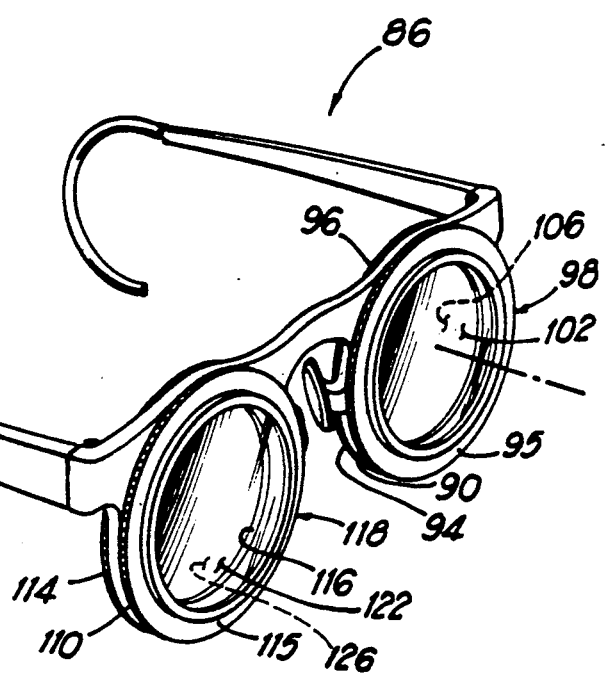
FIG. 4 is a perspective view of temporary spectacles designed to use the lens system associated with the present invention.

FIG. 4 illustrates a pair of spectacles 86 embodying the present invention. Such spectacles 86, which may be substantially similar aesthetically to existing eyeglasses, operate virtually identically to trial frames 14. In place of the knobs and rods shown in FIGS. 2-3, however, thumb wheels or knurled, ribbed, or otherwise rough surfaces 90 and 94 on lens rings 95 and 96 associated with right spectacle frame 98 may be used by the wearer to rotate cylinder, sphero-cylinder, or other lenses 102 and 106 as needed for obtaining the optimal visual acuity for the right eye. Similar thumb wheels or knurled, ribbed, or rough surfaces 110 and 114 on lens rings 115 and 116 associated with left spectacle frame 118 allow for continuous correction of optical errors associated with the patient's left eye. Spectacles 86 are particularly useful for persons whose refractive error is changing relatively rapidly over a short time period, such as those recovering from cataract or corneal transplant surgery, and who therefore cannot practically use conventional eyeglasses or contact lenses. Such users may merely adjust the positions of lenses 102, 106, 122, and 126 as their refractive error changes.

Although spectacles 86 and trial frames 14 may be designed to operate similarly, the weight and unwieldiness of conventional trial frames make them impractical for use as temporary eyeglasses. Consequently, spectacles 86 typically comprise right and left spectacle frames 98 and 118, respectively, made of lightweight plastic, metal, or other suitable material. Lenses 102, 106, 122, and 126 also may be made of lightweight plastic or other material, as use of four conventional glass lenses may make the spectacles 86 too heavy for comfortable wear. Spectacles 86 similarly typically lack many of the features of conventional trial frames designed to adjust single frames to fit a wide variety of wearers, as each frame may be designed to fit a particular wearer or group.

Figure 5:
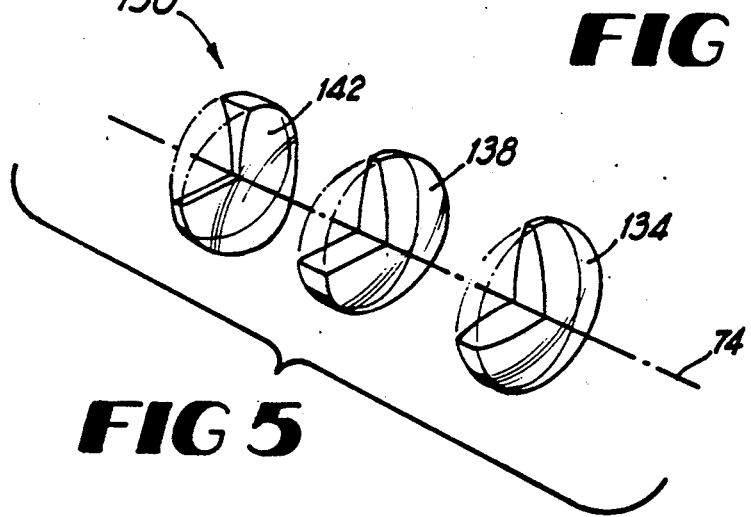
FIG. 5 is a perspective view of an alternative lens system associated with the present invention.

FIG. 5 details an alternative lens system 130 associated with the present invention which includes one sphero-cylinder lens 134 and two independently rotatable cylinder lenses 38 and 142. In one embodiment lens 134 is a $+0.75+3.25\times157°$ sphero-cylinder, one of lenses 138 and 142 is a $-2.50\times180°$ cylinder, and the other of lenses 138 and 142 is a $-2.50\times135°$ cylinder. Lens system 130 is not so limited, however, and may be composed alternatively of lenses having powers proportional (including both positive and negative factors and multiples) to those recited above or of cylinder lenses 138 and 142 having opposite signs (as shown in FIG. 5) if a compensating alteration is made to lens 134. In accordance with the present invention cylinder lenses 138 and 142 may be rotated from 0°-360°, while lens 134 may be rotated either ±90°. Like lens system 10, system may be utilized in a variety of devices used to measure or correct astigmatism, including refractors, temporary spectacles, and trial frames, and in oculars of microscopes, binoculars, or other similar devices as discussed earlier. If lens system 130 is to be used in trial frames 14, however, auxiliary lens holder 20 or accessory clip 76 should be modified to allow ±90° independent rotation of sphero-cylinder lens 134.

Chart 1 details some of the resultant crossed-cylinder powers achievable using lens system 130 described above, with lens 134 in its unrotated position and lenses 138 and 142 rotated ±90°.

CHART 1
GENERATED CROSSED CYLINDER POWERS
Lens 134: +0.75 +3.25 × 157°
Lens 138: −2.50 × 180°
Lens 142: −2.50 × 135°

| Rotation Angle for Lens 138 | Rotation Angle for Lens 142 | Resultant Crossed-Cylinder Power |
|---|---|---|
| −90° | −90° | +7.07 × 158° |
| −90° | −60° | +8.09 × 166° |
| −90° | −30° | +7.25 × 175° |
| −90° | 0° | +5.00 × 180° |
| −90° | +30° | +3.09 × 168° |
| −90° | +60° | +4.56 × 153° |
| −90° | +90° | +7.07 × 158° |
| −60° | −90° | +4.56 × 162° |
| −60° | −60° | +6.02 × 173° |
| −60° | −30° | +5.88 × 5° |
| −60° | 0° | +4.33 × 16° |
| −60° | +30° | +1.82 × 17° |
| −60° | +60° | +1.95 × 157° |
| −60° | +90° | +4.56 × 162° |
| −30° | −90° | +3.09 × 147° |
| −30° | −60° | +3.77 × 168° |
| −30° | −30° | +3.49 × 7° |
| −30° | 0° | +2.51 × 30° |
| −30° | +30° | +1.30 × 67° |
| −30° | +60° | +1.82 × 118° |
| −30° | +90° | +3.09 × 147° |
| 0° | −90° | +5.00 × 135° |
| 0° | −60° | +4.33 × 150° |
| 0° | −30° | +2.51 × 164° |
| 0° | 0° | 0.00 × 0° |
| 0° | +30° | +2.51 × 105° |
| 0° | +60° | +4.33 × 119° |
| 0° | +90° | +5.00 × 135° |
| +30° | −90° | +7.28 × 140° |
| +30° | −60° | +6.84 × 150° |
| +30° | −30° | +4.87 × 157° |
| +30° | 0° | +2.51 × 150° |

CHART 1-continued
GENERATED CROSSED CYLINDER POWERS
Lens 134: +0.75 +3.25 × 157°
Lens 138: −2.50 × 180°
Lens 142: −2.50 × 135°

| Rotation Angle for Lens 138 | Rotation Angle for Lens 142 | Resultant Crossed-Cylinder Power |
|---|---|---|
| +30° | +30° | +3.55 × 128° |
| +30° | +60° | +5.94 × 130° |
| +30° | +90° | +7.28 × 140° |
| +60° | −90° | +8.17 × 148° |
| +60° | −60° | +8.40 × 157° |
| +60° | −30° | +6.84 × 164° |
| +60° | 0° | +4.33 × 164° |
| +60° | +30° | +3.85 × 146° |
| +60° | +60° | +6.12 × 142° |
| +60° | +90° | +8.17 × 148° |
| +90° | −90° | +7.07 × 158° |
| +90° | −60° | +8.09 × 166° |
| +90° | −30° | +7.25 × 175° |
| +90° | 0° | +5.00 × 180° |
| +90° | +30° | +3.09 × 168° |
| +90° | +60° | +4.56 × 153° |
| +90° | +90° | +7.07 × 158° |

Chart 1 clearly demonstrates the range of crossed-cylinder powers and angles obtainable using the lens system 130. As shown in Chart 1, rotation of lenses 138 and 142 by ±90° generates powers from 0.00 D to more than 8.00 D in all quadrants except the 45°-90° meridian, where only weak powers are produced. To generate the equivalent range of powers in that quadrant, however, one need merely rotate sphero-cylinder lens 134 by 90°.

The foregoing is provided for the purposes of illustration, explanation, and description of embodiments of the present invention. Modifications and adaptations to these embodiments will be apparent to those of ordinary skill in the art and may be made without departing from the scope and spirit of the invention.

I claim:

1. A ophthalmic lens system comprising:
   a. a first lens having an optical axis, a cylindrical component, and a first axis, which first axis defines the meridian of greatest lens power for the first lens;
   b. a second lens aligned with the optical axis and having a cylindrical component and a second axis, which second axis defines the meridian of greatest lens power for the second lens and is offset 45° from the first axis;
   c. a third lens having spherical and cylindrical components and aligned with the optical axis; and
   d. means for rotating the first and second lenses independently about the optical axis.

2. A lens system according to claim 1 in which the lens powers of the first and second lenses are equal.

3. A lens system according to claim 1 in which the ratio of the cylindrical component of the third lens to the lens power of each of the first and second lenses is approximately −1.3.

4. A lens system according to claim 1 in which the means for rotating each of the first and second lenses comprises a gear for engaging each of the first and second lenses.

5. A lens system according to claim 1 in which the first lens is of power −2.50×180° D, the second lens is of power −2.50×135° D, and the third lens is of power +0.75+3.25×157° D.

6. Trial frames comprising:
   a. right and left frames;
   b. a lens system mountable in each of the right and left frames, each of which lens systems comprises:
      i. a first lens having an optical axis; and
      ii. a second lens alignable with the optical axis; and
   c. means for rotating the first and second lenses independently about the optical axis comprising a gear for engaging the first lens.

7. Trial frames according to claim 6 in which the lens system further comprises a first rotary cell for containing the first lens and a first rack encircling the first rotary cell, which first rack is engaged by the gear.

8. Trial frames according to claim 7 in which the lens system further comprises a second rotary cell for containing the second lens and a second rack encircling the second rotary cell.

9. Trial frames according to claim 8 in which the rotating means further comprises a second gear which engage the second rack.

10. Trial frames according to claim 9 in which the first and second lenses are detachably contained in, respectively, the first and second rotary cells.

11. Trial frames according to claim 6 in which the right and left frames are adapted for use as adjustable spectacles.

12. Trial frames according to claim 6 in which the rotating means comprises means for rotating the first and second lenses through 360°.

13. Trial frames comprising:
   a. right and left frames;
   b. a lens system mountable in each of the right and left frames, each of which lens systems comprises:
      i. a first lens having an optical axis; and
      ii. a second lens alignable with the optical axis;
   c. means for rotating the first and second lenses independently about the optical axis; and
   d. means for determining the sum of the powers of the first and second lenses for any given angle of rotation of each lens.

14. Trial frames according to claim 13 in which the rotating means comprises means for rotating the first and second lenses through 360°.

* * * * *